US007655793B2

(12) United States Patent
Herzer et al.

(10) Patent No.: US 7,655,793 B2
(45) **Date of Patent: *Feb. 2, 2010**

(54) NUCLEIC ACID PURIFICATION METHOD

(75) Inventors: Sibylle Herzer, Flemington, NJ (US); Sudhakar Rao Takkellapati, Belle Mead, NJ (US); Rajesh Ambat, Edison, NJ (US)

(73) Assignee: GE Healthcare Bio-Sciences Corp., Piscataway, NJ (US)

(*) Notice: Subject to any disclaimer, the term of this patent is extended or adjusted under 35 U.S.C. 154(b) by 205 days.

This patent is subject to a terminal disclaimer.

(21) Appl. No.: 11/857,727

(22) Filed: Sep. 19, 2007

(65) Prior Publication Data

US 2008/0076911 A1 Mar. 27, 2008

Related U.S. Application Data

(60) Provisional application No. 60/826,916, filed on Sep. 26, 2006.

(51) Int. Cl.
*C07H 21/00* (2006.01)

(52) U.S. Cl. .................................................... 536/25.4

(58) Field of Classification Search ....................... None
See application file for complete search history.

(56) References Cited

U.S. PATENT DOCUMENTS

| | | | |
|---|---|---|---|
| 5,561,064 | A | 10/1996 | Marquet et al. |
| 5,567,807 | A | 10/1996 | Craig et al. |
| 5,660,984 | A | 8/1997 | Davis et al. |
| 5,707,812 | A | 1/1998 | Horn et al. |
| 5,801,237 | A | 9/1998 | Johansson |
| 5,856,192 | A | 1/1999 | Bloch |
| 5,866,428 | A | 2/1999 | Kim et al. |
| 5,990,301 | A | 11/1999 | Colpan et al. |
| 6,020,186 | A | 2/2000 | Henco et al. |
| 6,090,288 | A | 7/2000 | Berglund et al. |
| 6,310,199 | B1 | 10/2001 | Smith et al. |
| 6,410,274 | B1 | 6/2002 | Bhikhabhai |

FOREIGN PATENT DOCUMENTS

| | | |
|---|---|---|
| DE | 197 46 874 | 4/1999 |
| EP | 0616639 | 11/1998 |
| EP | 1 243 649 | 9/2002 |
| EP | 0992583 | 3/2003 |
| EP | 1125943 | 10/2004 |
| WO | WO 97/29825 | 8/1997 |
| WO | WO 00/69872 | 11/2000 |
| WO | WO01/27331 | 4/2001 |
| WO | WO03/080834 | 10/2003 |
| WO | WO 2004/101809 | 11/2004 |

OTHER PUBLICATIONS

Chiang, Chen-Li, et al., "Application of superparamagnetic nanoparticles in purification of plasmid DNA from bacterial cells". Journal of Chromatography B (2005) 822, p. 54-60.
Bosch, F. X. (1985). "Studies on the development of the charge heterogeneity of the influenza virus glycoproteins". Archives of Virology, 83, 311-317.
Endres, H. N., Johnson, J. A. C., Ross, C. A., Welp, J. K., Etzel, M. R. (2003). "Evaluation of an ion-exchange membrane for the purification of plasmid DNA". Biotechnology and Applied Biochemistry, 37, 259-266.
Ferreira, G. N. M., Cabral, J. M. S. & Prazeres, D. M. F. (2000). "Anion exchange purification of plasmid DNA using expanded bed adsorption". Bioseparation, 9(1), 1-6.
Ferreira, G. N. M., Cabral, J. M. S., & Prazeres, D. M. F., (2000). "Studies on the Batch Adsorption of Plasmid DNA onto Anion-Exchange Chromatographic Supports". Biotechnology Progress, 16(3), 416-424.
Sambrook, J., Fritsch, E. F. & Maniatis, T. (1989). "Molecular Cloning: A Laboratory Manual". Cold Spring Harbor; New York: Cold Spring Harbor Laboratory Press.
Tseng, W. C., Ho, F. L. (2003). "Enhanced purification of plasmid DNA using Q-Sepharose by modulation of alcohol concentrations". Journal of Chromatography B, 791(1-2), 263-272.
Urthaler, J., Buchinger, W. & Necina, R. (2005). "Improved downstream process for the production of plasmid DNA for gene therapy". Acta Biochimica Polonica, 52(3), 703-711.
Delius, H., et al., "Separation of complementary strands of plasmid DNA using the biotin-avidin system and its application to the heteroduplex formation and RNA/DNA hybridizations in electron microscopy". Nucleic Acids Research (1985), 13(15) 5457-5469.

*Primary Examiner*—Lawrence E Crane
(74) *Attorney, Agent, or Firm*—Yonggang Ji

(57) ABSTRACT

Disclosed is a process for separating and/or purifying a nucleic acid by elution of the nucleic acid from anion exchange resins under conditions of high salt concentration and the presence in the eluant of an additive comprising guanidine, or a guanidine-like derivative. The process allows high recovery of nucleic acids from anion exchange resins without impairing the nucleic acid stability as compared with conventional ion exchange chromatographic procedures.

16 Claims, 9 Drawing Sheets

Agarose Gel

Real-time PCR

NUCLEIC ACID PURIFICATION METHOD

CROSS-REFERENCE TO RELATED APPLICATIONS

This application claims priority to U.S. provisional patent application No. 60/826,916 filed Sep. 26, 2006; the entire disclosure of which is incorporated herein by reference in its entirety. This application is related to co-pending U.S. patent application Ser. No. 11/857,882, filed Sep. 19, 2007, which claims priority to U.S. provisional patent application No. 60/826,924 filed Sep. 26, 2006. This application is also related to co-pending U.S. patent application Ser. No. 11/857,468, filed Sep. 19, 2007, which claims priority to U.S. provisional patent application No. 60/826,913 filed Sep. 26, 2006. U.S. patent application Ser. Nos. 11/857,882 and 11/857,468 and this current application are commonly owned by GE Healthcare Bio-Sciences Corp., and contain overlapping subject matter.

FIELD OF THE INVENTION

This invention relates generally to methods for separating nucleic acids such as genomic DNA, plasmid DNA and mRNA from contaminating cellular components such as proteins, lipids, soluble membrane components and the like. In particular, the invention relates to the improved recovery of nucleic acids from anion exchange chromatography media in either batch or packed mode by the addition of guanidine or guanidine-like derivatives in the presence of salt.

BACKGROUND OF THE INVENTION

The last three decades has seen considerable effort in the development of improved methods for the isolation and purification of nucleic acids from biological sources. This has been due mainly to the increasing applications of nucleic acids in the medical and biological sciences. Genomic DNA isolated from blood, tissue or cultured cells has several applications, which include PCR, sequencing, genotyping, hybridization and southern blotting. Plasmid DNA has been utilized in sequencing, PCR, in the development of vaccines and in gene therapy. Isolated RNA has a variety of downstream applications, including blot hybridization, in vitro translation, cDNA synthesis and RT-PCR.

The analysis and in vitro manipulation of nucleic acids is typically preceded by a nucleic acid isolation step in order to free the nucleic acid from unwanted contaminants which may interfere with subsequent processing procedures. For the vast majority of procedures in both research and diagnostic molecular biology, extracted nucleic acids are required as the first step. In a typical DNA extraction protocol, cells or homogenized tissue samples containing the nucleic acid of interest are harvested and lysed using standard methods, for example using enzymes such as Proteinase K and lysozyme; detergents, such as SDS, Brij, Triton X100, or using other chemicals such as sodium hydroxide, guanidium isothiocyanate, etc. (See for example, Sambrook et al, Molecular Cloning—A Laboratory Manual 2nd edition 9.14 (New York: Cold Spring Harbor Laboratory 1989). Following removal of the cellular debris, the crude lysate is treated with organic solvents such as phenol/chloroform to extract proteins. RNA may be removed or reduced if required by treatment of the enzymes such as RNAse. However, the presence of contaminants such as salts, phenol, detergents and the like can interfere with many downstream manipulations for which the nucleic acid is intended.

Currently several procedures are available for the chromatographic purification of DNA (genomic and plasmid) and RNA, for example, by employing silica based membrane purification, size exclusion chromatography, reversed phase chromatography, gel filtration, magnetic bead based purification, or ion-exchange chromatography. Ion exchange chromatography is one of the most commonly used separation and purification methods and has been used for purification of plasmid DNA, genomic DNA and RNA. See for example, U.S. Pat. No. 6,410,274 (Bhikhabhai), U.S. Pat. No. 6,310,199 (Smith et al), U.S. Pat. No. 6,090,288 (Berlund et al), U.S. Pat. No. 5,990,301 (Colpan et al), U.S. Pat. No. 5,856,192, U.S. Pat. No. 5,866,428 (Bloch), U.S. Pat. No. 5,801,237 (Johansson), EP 1125943 b1 (Macherey, Nagel GmbH & Co) EP 992583 B1, EP 616639 (Qiagen), U.S. Pat. No. 5,707,812, U.S. Pat. No. 5,561,064 (Vical Inc.).

While anion exchange chromatographic procedures for the purification of nucleic acids have been extensively referenced, one of the shortcomings of current protocols is the impaired recovery of nucleic acid during the elution step, (Endres, H. N. et al, Biotechnol. Appl. Biochem., (2003), 37(3), 259-66; Prazeres, D. M. et al, J. Chromatog. A. (1998), 806(1), 31-45; Urthaler J. et al, Acta Biochim. Pol., (2005), 52(3), 703-11; Ferreira, G. N. et al, Bioseparation, (2000), 9(1), 1-6; Ferreira, G. N., et al, Biotechnol. Prog., (2000), 16(3), 416-24. Addition of organic agents such as polyols and alcohols during adsorption and desorption has been shown to improve selectivity and recovery during anion exchange purification of DNA (Tseng, W. C. et al, J. Chromatogr. B Analyt. Technol. Biomed. Life Sci., (2003), 791(1-2), 263-72). However, there appear to be no reports that specifically address the recovery issues often seen during DNA desorption from anion exchange resins. The present invention addresses this problem since it relates to improving recoveries of bound DNA from anion exchange resins. In particular, the invention allows improved desorption of the DNA from the solid support without further manipulation of the protocol.

Plasmid DNA, genomic DNA and RNA have similar charge properties to one another and are polyanions having high charge density. Binding to positively charged ion exchange resins is therefore possible in the presence of up to 0.7M sodium chloride, depending on the length and conformation of the nucleic acid to be adsorbed. An increase in nucleic acid length as well as double stranded conformation results in an increase in binding strength between the nucleic acid and the anion exchanger. However, this effect is only proportional to nucleic acid length up to about 2 kilobases. The very strong interaction between the negatively charged phosphate backbone of the nucleic acid and ion exchange resin hampers elution of the nucleic acid using conventional methods, where a simple increase in ionic strength of the salt eluant is sufficient for recovery of 70-100% of the bound material. However, in the case of longer chain nucleic acids, an increase in ionic strength up to 3M salt only allows recoveries of 20-50% of the bound nucleic acid. Recovery of the remaining bound material can be accomplished with a combination of high salt concentration and elevated pH using sodium hydroxide. However, sodium hydroxide is not only caustic, but may also lead to irreversible denaturation of nucleic acids and degradation over time.

BRIEF DESCRIPTION OF THE INVENTION

Surprisingly, it has now been found that nucleic acids can be efficiently eluted from anion exchange resins under conditions of high salt concentration and the presence in the eluant of an additive comprising guanidine, or a guanidine-like derivative, the pH of the eluant being suitably in the range of about pH 9 to about pH 13, and more preferably in the range of about pH 10.5 to about pH 11.6. The addition of guanidine or a guanidine-like derivative to the elution solution has been shown to improve recovery of nucleic acids from anion exchange resins from 20-50% to 70-95%.

Thus, in a first aspect the present invention provides a process for separating and/or purifying a nucleic acid, comprising:

a) contacting an aqueous solution containing the nucleic acid with an anion exchanger bound to a solid support matrix under conditions such that the anion exchanger binds the nucleic acid; and b) eluting the anion exchanger with an aqueous mobile phase comprising a nucleic acid elution salt solution;

characterised in that the elution solution comprises an additive having the formula (I):

(I)

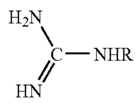

wherein:

R is a moiety selected from the group consisting of hydrogen, a lower alkyl, optionally substituted by amino, and the group:

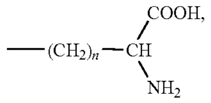

where n is 1, 2 or 3;

wherein the presence of the additive in the elution solution provides an increase in the recovery of nucleic acid from the anion exchanger, as compared with the recovery of the nucleic acid from the same anion exchanger and in the absence of the additive in the elution solution, all other conditions being equal.

Thus, the present invention provides a method for the use of a compound as an additive to the elution solution to allow high recovery of nucleic acids from anion exchange resins without impairing the nucleic acid stability as compared with conventional ion exchange chromatographic procedures. Nucleic acids, consist of a chain (or a paired chain of deoxyribose phosphate monomers covalently linked via phosphodiester bonds, each sugar phosphate moiety carrying a single aromatic heterocyclic base: adenine (A), guanine (G), cytosine (C), thymine (T) found solely in DNA), and uracil (U) found solely in RNA). In aqueous solutions of a pH>2, the highly soluble hydrophilic sugar-phosphate polymer backbone contributes one negative charge for each phospho-diester group, with the exception of the terminal phospho-monoester, which may carry up to two negative charges. DNA is thus a polyanion, where the net negative charge of the nucleic acid molecule is related directly to chain length. Nucleic acids therefore, display strong binding affinities to anion exchange resins such that a high salt concentration in the elution solution is required to efficiently remove the nucleic acid from the resin. Compounds such as guanidine, guanidine-like compounds such as methyl- and ethyl-guanidine, and compounds containing a guanidinium moiety such as arginine) mediate interaction with nucleic acids through electrostatic interactions and hydrogen bonding.

The positive impact of guanidine and guanidine-like compounds particularly arginine on recovery of nucleic acids from anion exchange resins is most pronounced at alkaline pH, for example, between about pH 9 and about pH 13, more particularly at pH values between about 10 and 12. A pH range of between about 10.5 and 11.6 appears to provide optimum recovery. Recovery of nucleic acids is highest when arginine or guanidine carbonate is added to the elution solution. Without being bound by theory, one of the unique properties of the guanidinium group is its delocalized positive charge property which is due to the conjugation between the double bond and the nitrogen lone pairs. The guanidinium group is able to form multiple hydrogen-bonds preferentially with guanine bases, which may act to cause local deformation of the nucleic acid structure, which change in conformation of nucleic acids contributes to a change in desorption kinetics thereby favouring high recoveries of nucleic acids during anion exchange chromatography. Macromolecules are known to bind to adsorptive surfaces through multiple points of attachment creating microenvironments on chromatography media surfaces, which allow adsorption that can become close to irreversible with conventional desorption techniques. While traditional anion exchange chromatography allows the elution of bound molecule from the positively charged ligand through an increase in competing salt anions, it has been observed that elution of nucleic acids, especially high molecular weight (HMW) nucleic acids (above 0.1 kilobases), is not efficient with salt anions alone. It has also been observed that the cation used as a counter ion, as well as the pH of elution has an effect on recovery of HMW nucleic acids, the use of strongly alkaline (such as with sodium hydroxide) may be detrimental to recovery because of the co-elution of contaminants and detrimental effects on product stability.

In one embodiment, the additive is a compound having the formula (I)

(I)

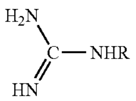

(and more particularly the carbonate or bicarbonate salt thereof), where R is selected from H, and lower alkyl, optionally substituted by amino. Suitably, lower alkyl is a $C_1$ to $C_4$ alkyl group, for example methyl, ethyl, propyl and butyl, preferably, methyl or ethyl. Where R is an amino-substituted lower alkyl group, examples of the compounds according to formula (I) include 2-aminoethyl-guanidine, 3-aminopropyl-guanidine and 4-aminobutyl-guanidine (agmatine). In a particularly preferred embodiment, R is hydrogen, thus compound (I) is guanidine, as its carbonate or bicarbonate salt.

In a second embodiment, the additive is a compound having the formula (I):

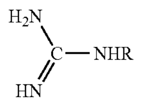

(I)

wherein R is the group:

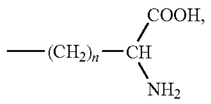

where n is 1, 2 or 3, preferably 3. In this case, the additive is arginine, suitably L-arginine, D-arginine, or a mixture of both optical isomers.

In embodiments according to the invention, it is preferred that the guanidine and guanidine-like compound is present as an additive in the elution solution at a concentration of between 0.1M and 2M, preferably between 0.25M and 0.5M. The elution solution will typically comprise a salt solution, suitably between about 0.7M and 3M to which the additive is added. Suitably, the pH of the aqueous mobile phase is between about pH 9 and about pH 13, the preferred range of pH being between about pH 10 and about pH 12, more preferably between about pH 10.5 and about pH 11.6.

The term "nucleic acid" as used herein refers to any DNA or RNA molecule, or a DNA/RNA hybrid, or mixtures of DNA and/or RNA. The term "nucleic acid" therefore is intended to include genomic or chromosomal DNA, plasmid DNA, amplified DNA, total RNA and mRNA. The process according to the present invention is particularly suitable for the preparation and/or purification of genomic DNA derived from complex mixtures of components derived from cellular and tissue samples from any recognised source, including normal and transformed cells, with respect to species (e.g. human, rodent, simian), tissue source (e.g. brain, liver, lung, heart, kidney skin, muscle) and cell type (e.g. epithelial, endothelial, blood); or for the purification of plasmid DNA derived from *E. coli* and yeast.

Furthermore, the present method is suitable for the preparation and/or purification of genomic DNA having a size of from about 0.1 kilo-bases to about 200 kilo-bases, or of plasmid DNA, cosmid, BAC or YAC DNA. The present invention is useful for purifying plasmid DNA and cosmid DNA, in particular for downstream applications in molecular biological research, such as cloning and sequencing, gene therapy and in diagnostic applications both in vivo and in vitro.

Anion exchange resins suitable for use with methods of the present invention include both strong anion exchangers and weak anion exchangers, wherein the anion exchange resin suitably comprises a support carrier to which charged or chargeable groups have been attached. The ion exchange resin may take the form of a bead, a membrane or a surface. Examples of strong anion exchange resins include Q-Sepharose fast flow resin, Q-Sepharose XL and CaptoQ. Examples of weak ion exchange resins include ANX fast flow resin and DEAE Sephadex A-25 resin (GE Healthcare).

By employing an additive of formula (I) in the aqueous mobile phase it is possible to increase recovery of nucleic acid from the anion exchanger of at least 40% and typically between about 40% and about 400%, as compared with the recovery of said nucleic acid from the same anion exchanger and in the absence of the additive in the elution solution, all other conditions being equal.

Other features and advantages of the invention will be apparent from the following description of the preferred embodiments, and from the claims.

DETAILED DESCRIPTION OF THE PREFERRED EMBODIMENTS

Figure 1:
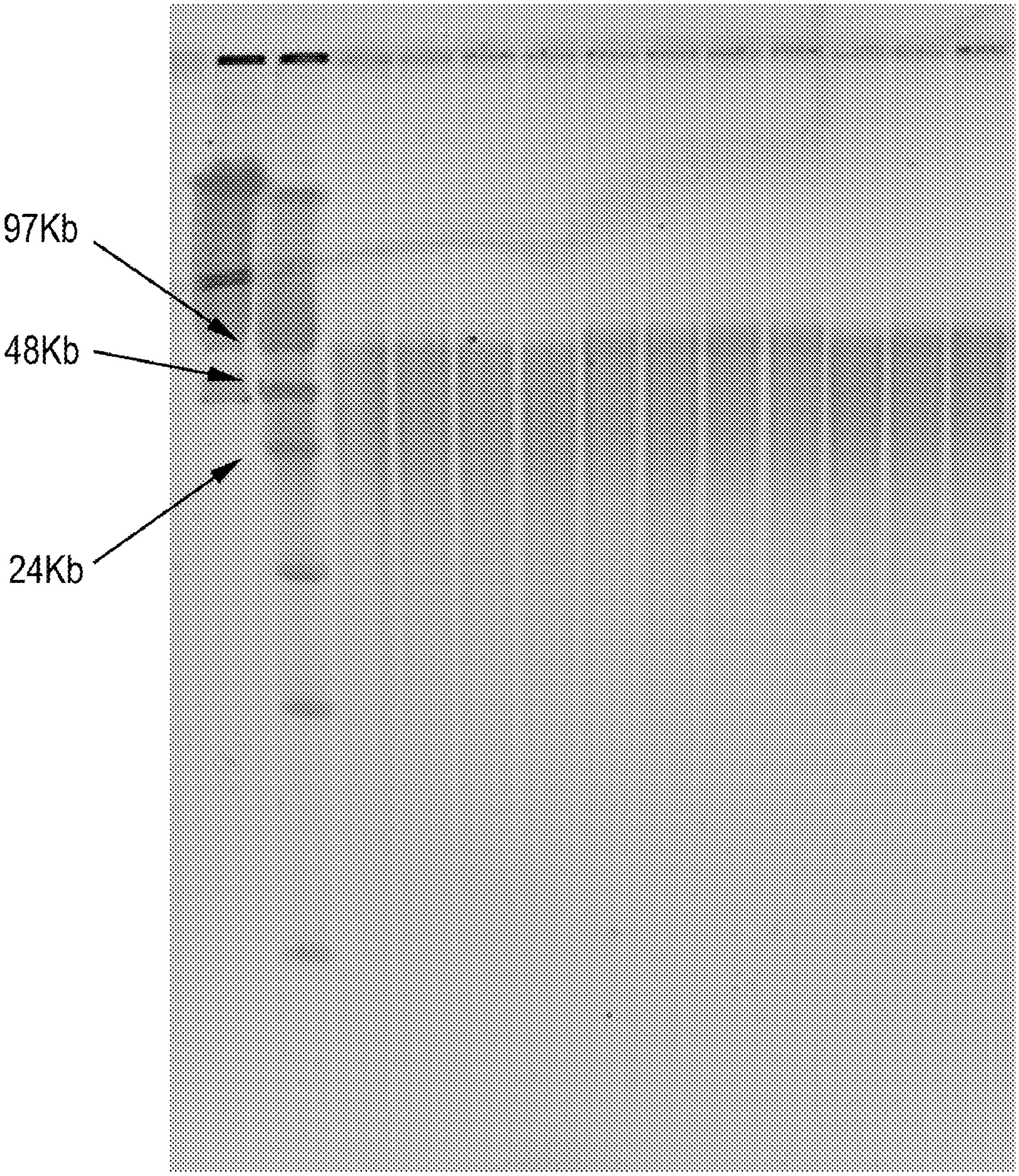
FIG. 1 shows pulse-field gel electrophoresis analysis of purified genomic DNA from 11 different human blood samples. The DNA was isolated according to protocol (a). The left two lanes contain molecular weight markers with the relevant sizes labeled. It can be seen that the purified genomic DNA are all of large size.

The following examples serve to illustrate the DNA purification processes according to embodiments of the present invention and are not intended to be limiting.

(A) Protocols Used in the Examples (a) Isolation of Genomic DNA from Blood

Genomic DNA isolation from blood is done in 2 steps. The first step is the lysis of blood and the second step is purification of genomic DNA using ion-exchange column chromatography.

Lysis: This process involved 2 steps. First white blood cells are isolated and then the isolated white blood cells are lysed using lysis solution. The protocol used for the isolation of white blood cells and lysis of white blood cells is as follows. Five ml of blood is used as an example here. However, the protocol can be adjusted accordingly based on the amount of blood used.

1. Add 5 ml of whole blood to a 50 ml conical centrifuge tube.

2. Add 5 ml of pre-chilled Lysis1 solution and 15 ml of chilled water to the sample. Place the tubes in a rack and mix well by inverting the tubes 10-15 times.

3. Incubate at ambient temperature for 10 minutes.

4. Centrifuge at 1500×g for 10 minutes.

5. Discard the supernatant into a waste container containing diluted bleach solution (or follow appropriate safety precautions as recommended by the EHS) without disturbing pellet.

6. Add 1 ml of Lysis1 solution and 3 ml of water to the centrifuge tube and re-suspend the pellet by vortexing briefly.

7. Centrifuge at 5000×g for 10 minutes.

8. Discard the supernatant carefully without disturbing the white blood cell pellet.

9. Re-suspend the white blood cell pellet in 5 ml of Lysis2 solution by vortexing at highest speed for 30 sec to 1 min.

10. Add 50 µl of Proteinase K (20 mg/ml) (AG Scientific), vortex briefly and incubate at ambient temperature for 20 minutes.

11. Add 5 ml of Loading Solution to the centrifuge tube and mix well by swirling the tube and load this solution on the purification column.

Purification: The purification process also includes a de-salting process (steps 17-21).

12. Remove the cap from the top of an ion exchange purification column (approximately 1.5 ml of ion exchange resin in a plastic tube, packed using an automated process). Discard the solution by decanting. Cut the closed end of the column at the notch and place the columns in 50 ml centrifuge tubes using column adaptors.

13. Transfer the lysis solution obtained from step 11 above to the column and allow it to flow completely through the resin by gravity.

14. Apply 5 ml of Loading Solution to the column.

15. When all the Loading Solution passes through the resin, place the columns in fresh 50 ml centrifuge tubes.

16. Add 2.5 ml of Elution Solution to the column and collect the product in the eluate.

Desalting:

17. Remove the cap of desalting column and discard the solution. Cut the closed end of the column at notch and place the column in a centrifuge tube using the adaptor.

18. Equilibrate the column by applying 25 ml of 1× TE buffer (10 mM Tris-HCl, pH 8.0, 1 mM EDTA). This can be accomplished by using LabMate PD-10 buffer reservoir (GE Healthcare) in one step.

19. Transfer the eluate (2.5 ml) from the purification step 16 to desalting column and allow it to flow by gravity.

20. When the solution has completely entered the gel bed, place the column in fresh 50 ml centrifuge tube.

21. Add 3.5 ml of 1×TE buffer to each column and collect the eluate containing genomic DNA. The desalted samples are now ready for quantitation and downstream applications.

(b) Isolation of Genomic DNA from Tissue Samples

The tissue sample is prepared by the following steps. It is critical to have a completely homogenized sample to obtain good yield of genomic DNA from the purification process.

1. Weigh approximately 100 mg of tissue by slicing into very fine pieces.

2. Wash the tissue with 1×PBS buffer. Add 1 ml of 1×PBS buffer, vortex and centrifuge at 1000 RPM for 1 min. Discard the washing and remove any traces of buffer left in the tube using a pipette.

3. Add 0.5 ml of 1×PBS buffer and homogenize the sample by handheld homogenizer.

Tissue samples so prepared are subjected to the following steps for the isolation of genomic DNA. Steps 4-7 are for sample lysis; steps 8-12 are for purification; and steps 13-17 are for de-salting.

4. Add 0.5 ml of Lysis Solution to the homogenized sample (PBS and lysis Solution in 1:1 ratio) and vortex at the highest possible speed for 20-30 sec.

5. Add 50 µl of proteinase K (20 mg/ml) solution, vortex briefly and incubate at 60° C. for 1.5 hours.

6. After the incubation period, cool the reaction tubes in an ice bath for 3 min. Add 20 µl of RNAse A solution (20 mg/ml) and incubate at 37° C. for 15 min.

7. Dilute the crude lysate with 4 ml of DNAse free water and 5 ml of Loading Solution and centrifuge at 5000×g for 15 min to pellet particulates.

Purification:

8. Remove the cap from the top of purification column. Discard the solution by decanting. Cut the closed end of the column at the notch and place the columns in 50 ml centrifuge tubes using column adaptors.

9. Transfer the lysis solution to the column and allow it to flow completely through the resin by gravity.

10. Apply 5 ml of Loading Solution to the column.

11. When all the Loading Solution passes through the resin, place the columns in fresh 50 ml centrifuge tubes.

12. Add 2.5 ml of Elution Solution to the column and collect the product in the eluate.

Desalting:

13. Remove the cap of desalting column and discard the solution. Cut the closed end of the column at notch and place the column in a centrifuge tube using the adaptor.

14. Equilibrate the column by applying 25 ml of 1×TE buffer. This can be accomplished by using LabMate PD-10 buffer reservoir.

15. Transfer the eluate (2.5 ml) from the purification step 12 to desalting column and allow it to flow by gravity.

16. When the solution completely entered the gel bed, place the column in fresh 50 ml centrifuge tube.

17. Add 3.5 ml of 1×TE buffer to each column and collect the eluate containing genomic DNA. The desalted samples are now ready for quantitation and downstream applications.

(c) Isolation of Genomic DNA from Cell Cultures

Cell cultured cells are collected and lysed according to the protocol below. The purification and desalting is done as described in protocol (b) ("Isolation of genomic DNA from tissue samples") above.

1. Wash between $1\times10^7$ and up to $2.0\times10^7$ cells with 1×PBS buffer (2×5 ml). Suspend the cells in 5 ml of 1×PBS buffer and centrifuge at 2000×g for 10 min. Decant the buffer carefully from the pellet and repeat the process once more.

2. Re-suspend the cell pellet completely in 1 ml of 1×TE Buffer by vortexing for 30 seconds to 1 minute.

3. Add 4.5 ml of Lysis Solution and vortex for 15-30 sec.

4. Add 50 μl of Proteinase K (20 mg/ml) and vortex briefly (2 sec).

5. Incubate at 60° C. for 1-2 hours.

6. Cool the tube in an ice bath for 2 min and add 20 ul of RNase A (20 mg/ml).

7. Incubate at 37° C. for 15 min.

(d) Quantitation of the Purified Genomic DNA Samples

Quantitation of the purified genomic DNA samples was achieved with a UV spectrophotometer, using 1×TE Buffer pH8.0 as the blank and 1 cm path length cuvettes. Readings of three samples were taken at A260, A280 and A320. Yield of DNA (μg)=A260×50 μg×Eluted sample volume (3.5 ml).

(e) Detailed Composition of Solutions Used in the Protocols (i) Blood gDNA Protocol:

Lysis1 solution: 30 mM Tris-HCl, 10 mM Magnesium chloride, 2% Triton X 100 and 0.6M sucrose.

Lysis2 solution: 20 mM Tris-HCl, 20 mM EDTA, 20 mM sodium chloride and 0.1% SDS.

Loading solution: 700 mM sodium chloride, 50 mM Tris and 1 mM EDTA.

(ii) Tissue Protocol:

Lysis solution: 20 mM Tris-HCl, 20 mM EDTA, 100 mM sodium chloride and 1% SDS.

Loading solution: 700 mM sodium chloride, 50 mM Tris and 1 mM EDTA.

(iii) Cell Culture Protocol:

Lysis Solution: 20 mM Tris-HCl, 20 mM EDTA, 100 mM sodium chloride and 1% SDS.

(B) Evaluation of Various Solutions for Genomic DNA Elution

In an effort to find an optimal elution solution for genomic DNA purification, high ionic salt strength solutions were tested for elution of genomic DNA from the bound anion exchanger.

As an example, ANX Sepharose fast flow (high sub) resins were used here. These resins are very stable over a wide pH range (3-13), with an average particle size of 90 μm (We have subsequently tested other anion exchange resins and found they work well too). The columns were pre-packed using a salt solution having similar strength as the sample loading solution, with suitable anti-microbial agent (e.g. ethanol or kethon). This eliminates the need for column equilibration prior to loading of the sample in loading solution for binding of the nucleic acid.

The source cell used here was human blood and the blood protocol described in (A) (a) above was followed. We found that even when a salt concentration of 2 to 3M was used it did not significantly improve the recovery of genomic DNA from the ion-exchange columns. After elution all the samples were desalted using NAP-10 or NAP-25 columns (GE Healthcare) and the DNA was quantified using UV spectrophotometer. To identify a buffer or a solution which could provide better recovery, different combinations of salts were evaluated.

The following elution buffer/solution combinations were evaluated for genomic DNA elution in individual experiments.

1. 50 mM Tris-HCl, pH 8.0, 1 mM EDTA, 2000 mM NaCl 2. 50 mM Tris-HCl, pH 8.0, 1 mM EDTA, 2000 mM NaCl+0.2 M sodium carbonate 3. 50 mM Tris-HCl, pH 8.0, 1 mM EDTA, 2000 mM NaCl+0.2 M sodium perchlorate 4. 50 mM Tris-HCl, pH 8.0, 1 mM EDTA, 2000 mM NaCl+0.2 M sodium bicarbonate 5. 50 mM Tris-HCl, pH 8.0, 1 mM EDTA, 2000 mM NaCl+0.2 M magnesium chloride 6. 2M Sodium iodide 7. 2M Sodium perchlorate 8. 3M Ammonium acetate 9. 3M Ammonium acetate+0.2M sodium bicarbonate 10. 3M Ammonium acetate+0.2M sodium carbonate 11. 3M Ammonium acetate+0.2M sodium biborate 12. 3M Ammonium bicarbonate 13. 3M Sodium bicarbonate (not dissolved completely)

14. 3M Sodium carbonate 15. 3M Sodium phosphate (not dissolved completely, precipitates)

16. 50 mM Tris-HCl, pH 8.0, 1 mM EDTA, 2000 mM NaCl+25 mM sodium hydroxide 17. 50 mM Tris-HCl, pH 8.0, 1 mM EDTA, 2000 mM NaCl+50 mM sodium hydroxide 18. 50 mM Tris-HCl, pH 8.0, 1 mM EDTA, 2000 mM NaCl+75 mM sodium hydroxide 19. 50 mM Tris-HCl, pH 8.0, 1 mM EDTA, 2000 mM NaCl+100 mM sodium hydroxide 20. 50 mM Tris-HCl, pH 8.0, 1 mM EDTA, 2000 mM NaCl+75 mM Lithium hydroxide 21. 2M Salt+500 mM L-Arginine 22. 1M sodium chloride+1M sodium carbonate Representative results are shown below in Table 1. From the data it is clear that 2M salt solution itself elutes less than half of the genomic DNA that could be eluted with a combination of salt and sodium hydroxide, or salt and arginine.

TABLE 1

Representative elution solution combinations and genomic DNA yields

| Eluant | Yield | Purity |
|---|---|---|
| 2M Salt buffer | 32 μg | 1.80 |
| 2M Salt buffer + 50 mM NaOH | 72 μg | 1.87 |
| 2M Salt buffer + 75 mM NaOH | 79 μg | 1.89 |
| 2M Salt buffer + 75 mM LiOH | 76 μg | 1.92 |
| 2M Salt buffer + 100 mM NaOH | 72 μg | 1.88 |
| 2M Salt buffer 500 mM NaOH | 74 μg | 1.8 |
| 2M Salt + 1M Sodium carbonate | 56 μg | 1.76 |

Recovery of the remaining bound material can be accomplished with a combination of high salt concentration and elevated pH using sodium hydroxide. However, sodium hydroxide is not only caustic, but may also lead to irreversible denaturation of nucleic acids and degradation over time.

It has also been observed that the cation used as a counter ion, as well as the pH of elution has an effect on recovery of HMW nucleic acids, the use of strongly alkaline (such as with sodium hydroxide) may be detrimental to recovery because of the co-elution of contaminants and detrimental effects on product stability.

Since arginine, which has a carboxylic acid group and also a guanidinium group, was showing a dramatic effect in the elution process, we evaluated other amino acids and guanidinium salts and also the combination of amino acid and guanidinium salt to identify whether it is the carboxylic acid group or guanidinium group that contributes to the improved recovery. The results are summarized in Table 2.

TABLE 2

Evaluation of various amino acids and guanidinium salts for their effects in improving genomic DNA elution

| Eluant | Yield | Purity |
|---|---|---|
| 3M Salt buffer | 37 μg | 1.78 |
| 2M Salt buffer + 1M Sodium carbonate | 62 μg | 1.73 |
| 2M Salt buffer + 0.5M Arginine | 82 μg | 1.80 |
| 2M Salt buffer + 0.1M Arginine | 46 μg | 1.78 |
| 2M Salt buffer + 0.5M Aspartic acid | 39 μg | 1.63 |
| 2M Salt buffer + 0.5M Aspartic acid + 0.5M Guanidine HCl | 41 μg | 1.57 |
| 2M Salt buffer + 0.5M Guanidine | 39 μg | 1.64 |
| 2M Salt buffer 50 mM NaOH | 76 μg | 1.81 |

We noticed that the elution solutions which improve genomic DNA recovery and elution have a common feature, that is an elevated pH of around 10.5 to 11.5. It appears that improved elution of nucleic acids employing guanidinium is facilitated by the presence in the elution solution of carbonate (or bicarbonate). Based on this observation further experiments were performed to test the effect of elevated pH. We compared 2M sodium chloride with sodium carbonate or 2M sodium chloride with Tris base or arginine. The results obtained are given in Table 3.

TABLE 3

Evaluation of various solutions with similar pH for their effects on improving genomic DNA elution

| Eluant | Yield | Purity |
|---|---|---|
| 2M Salt buffer | 64 μg | 1.81 |
| 2M Salt buffer + 0.25M Arginine | 110 μg | 1.81 |
| 2M Salt buffer + 0.5M Arginine | 118 μg | 1.82 |
| 2M Salt buffer + 0.5M Sodium carbonate | 93 μg | 1.79 |
| 2M Salt buffer + 1M Sodium carbonate | 93 μg | 1.74 |
| 2M Salt buffer + 0.5M Tris base | 86 μg | 1.77 |
| 2M Salt buffer + 1M Tris base | 85 μg | 1.77 |
| 2M Salt buffer + 50 mM NaOH | 118 μg | 1.82 |
| 2M Salt buffer + 0.5M Arginine | 101 μg | 1.82 |
| 2M Salt buffer + 0.5M Arginine | 97 μg | 1.82 |

Based on the evaluation of several different solutions pH appears to play a critical role in the recovery of genomic DNA in addition to the salt strength. Combination of 1 to 2M sodium chloride, with 0.25M to 0.5M arginine, 0.5-1M sodium carbonate and 0.5-1M Tris can be used for improved elution.

Since elevated pH appeared to be the factor that helped recover higher amount of genomic DNA from the ion-exchange resins, several more combinations of salt with guanidine derivatives were evaluated as an elution solution, all of which provided higher pH for the elution solution.

1. 2M NaCl+0.2 M L-Arginine 2. 2M NaCl+0.5M Guanidine carbonate 3. 2M NaCl+0.5M Guanidine carbonate+0.5M Glycine 4. 2M NaCl+0.5M Guanidine carbonate+0.5M L-glutamic acid 5. 2M NaCl+0.5M Guanidine propionic acid The results clearly demonstrate that addition of arginine, guanidine carbonate or other guanidine derivatives such guanidine propionic acid to 1M to 2M sodium chloride solution has similar effects on the elution of genomic DNA from the ion-exchange resins (Table 4).

TABLE 4

Evaluation of additional solutions with similar pH for their effects in improving genomic DNA elution

| Eluant | Yield | Purity |
|---|---|---|
| 2M Salt buffer + 0.25M Arginine | 121 μg | 1.8 |
| 2M Salt buffer + 0.5M Guanidine carbonate | 128 μg | 1.8 |
| 2M Salt buffer + 0.5M Guanidine carbonate + 0.5M Glycine | 130 μg | 1.81 |
| 2M Salt buffer + 0.5M Guanidine carbonate + 0.5M L-Glutamic acid | 125 μg | 1.79 |
| 2M Salt buffer + 0.5M Guanidine propionic acid | 126 μg | 1.77 |

(C) Comparison of L-Arginine, Guanidine Carbonate and Potassium Carbonate in Elution Solution Since a combination of sodium chloride and sodium carbonate did provide some improvement in the recovery, a solution of potassium carbonate in combination with sodium chloride is evaluated, in comparison with guanidine carbonate and L-arginine. The pH of a solution of sodium chloride and sodium carbonate is not optimal for complete recovery of the nucleic acids from the ion-exchange resin. Since potassium carbonate will give higher pH solution, it is expected to give higher recovery of the nucleic acids from ion-exchange resins. Indeed a combination of sodium chloride and potassium carbonate did give a solution with higher pH and the elution profile compared well with a solution containing guanidine carbonate or arginine. The experimental details are similar to those of section (B) supra. Again, human blood was used as the genomic DNA source and the blood protocol described in (A) (a) was followed. The results are shown in Table 5.

TABLE 5

Evaluation of the effect of L-Arginine, Guanidine Carbonate and Potassium Carbonate in elution solutions

| Eluant | Yield | Purity |
|---|---|---|
| 1M NaCl + 0.5M L-Arginine | 146 | 1.77 |
| 1M NaCl + 0.5M Guanidine carbonate | 139 | 1.77 |
| 1M NaCl + 0.5M Potassium carbonate | 144 | 1.79 |

From the data in Table 5, it is clear that a sodium chloride solution containing potassium carbonate is equally effective in genomic DNA elution, when compared with a solution containing either guanidine carbonate or L-arginine, from ion-exchange resins. Based on the systematic evaluation of various additives, pH appears to play a critical role in the recovery of nucleic acid in addition to the salt strength. Combination of 1 to 2M sodium chloride, with 0.25 to 0.5M arginine, 0.5M potassium carbonate or 0.5M guanidine carbonate can be used for improved elution. 0.5 to 1M sodium carbonate or 0.5M to 1M Tris base can also be used to increase the elution as well.

(D) Genomic DNA Purification from Blood

Figure 2:
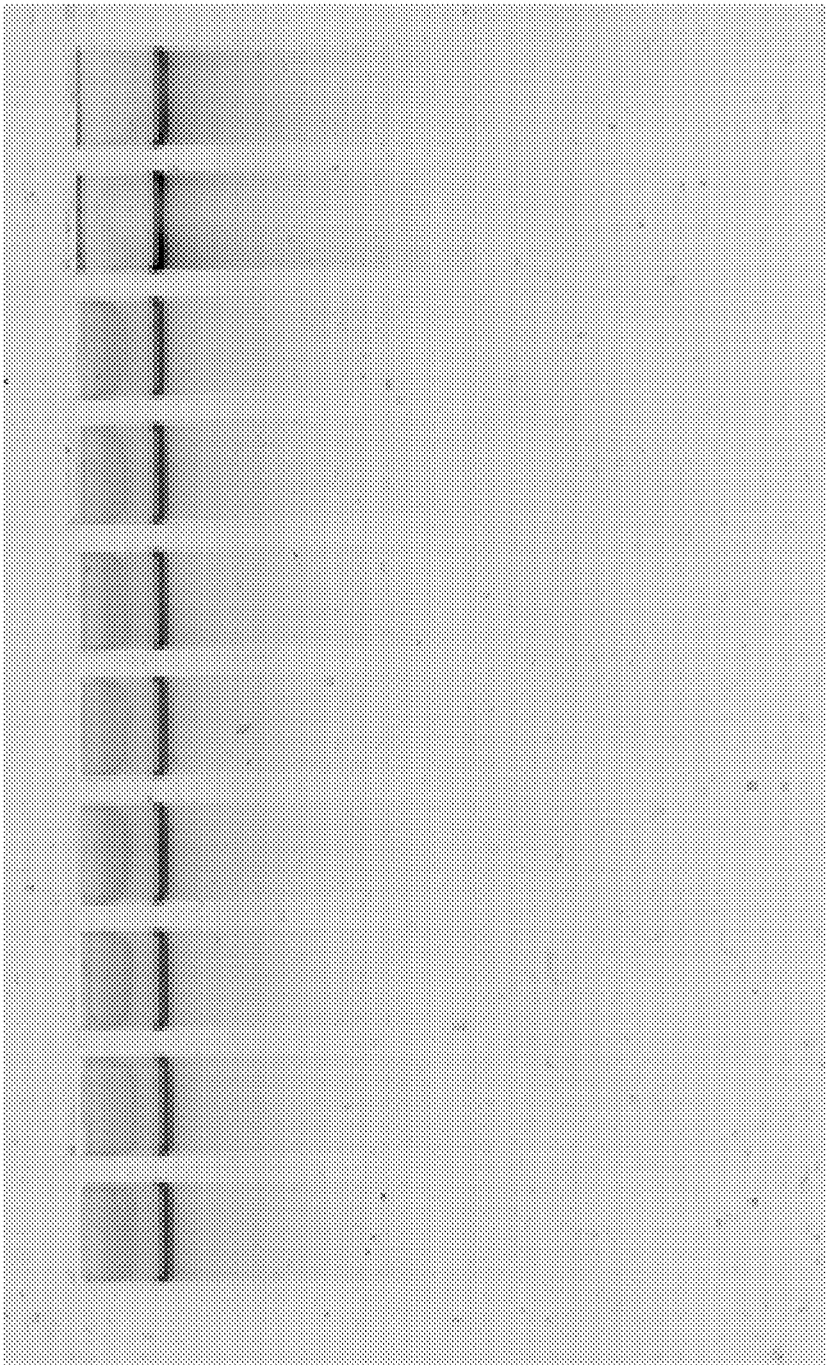
FIG. 2 shows an agarose gel image of 10 of the purified genomic DNA samples shown in FIG. 1. The samples contain no visible RNA contamination.
Figure 3:
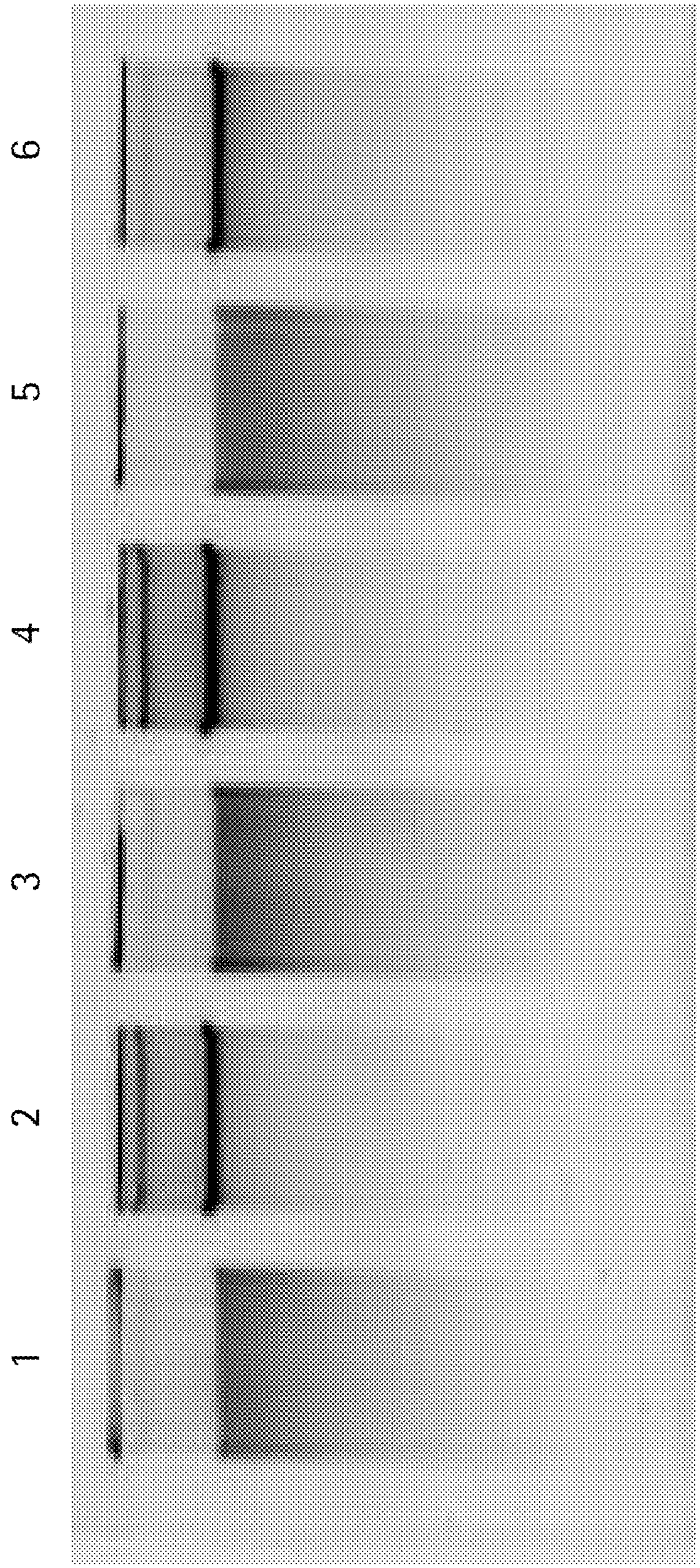
FIG. 3 is an agarose gel image that shows comparison of restriction enzyme (EcoRI) digested and un-digested genomic DNA from 3 of the purified genomic DNA samples shown in FIG. 1. Lanes 2, 4, 6 are undigested controls, while lanes 1, 3, 5 are samples that have been digested, respectively. All the samples can be completely digested, further demonstrating the purity of the samples.
Figure 4:
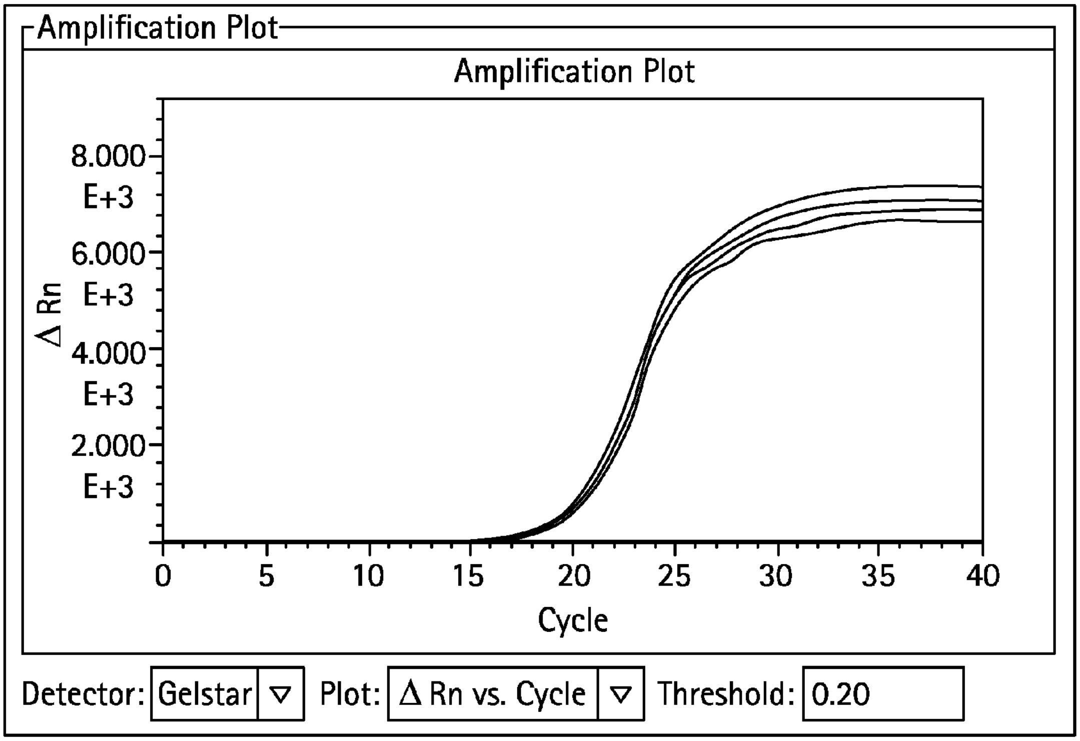
FIG. 4 shows real time PCR amplification results obtained from certain genomic DNA samples shown in FIG. 1. Very similar amplification profiles can be observed among the samples, further demonstrating the quality of the genomic DNA samples.

An 8 ml sample of human blood was lysed using the procedure described in the protocol section. The crude lysate was diluted with loading solution and loaded on the ion-exchange purification column. After all the solution passed through the resin an additional 5 ml of loading solution was added onto the column. When there was no more solution on the top of the resin, 2.5 ml of elution solution (1M sodium chloride+0.5M potassium carbonate) was added and the eluate containing genomic DNA was collected in a collection tube. The product obtained was desalted using NAP-25 column. The size of the genomic DNA isolated was determined by Pulse Field Gel Electrophoresis (FIG. 1). The purity of the product was assessed by UV spectrophotometry and by gel analysis (FIG. 2). The genomic DNA obtained by this method was also evaluated in downstream applications such as restriction digestion (FIG. 3), Multiplex PCR and Real Time PCR (FIG. 4).

By Pulse Field Gel Electrophoresis, it is clear that the purified genomic DNA from Blood is of large size (FIG. 1). The purity of the sample was examined by an agarose gel analysis (FIG. 2). It demonstrates that the genomic DNA isolated is pure and without RNA contamination.

The quality of the purified genomic DNA was assessed by several methods.

The DNA was subjected to restriction enzyme digest using EcoRI. Purified genomic DNA (250 ug) was digested with 40 units of the enzyme. The digested sample was analyzed on an agarose gel side-by-side with un-digested sample DNA. The gel image shows that all the genomic DNA was completely digested (FIG. 3, Lanes 2, 4, 6 represent the purified, un-digested genomic DNA, while Lanes 1, 3, 5 are samples digested with the enzyme).

The quality of the genomic DNA samples was indirectly measured by the efficiency in a multiplex PCR reaction. A long range multiplex PCR for the P450 genes were used for this test (CodeLink P450 protocol, GE Healthcare). Three amplicons from genes CYP2D6, CYP3A4, and CYP3A5 were amplified in a single reaction. The size in amplicons ranges from 335 bp to 2600 bp. The size and yield of the PCR products were determined via the Agilent Biolanalyzer 2100 and DNA 7500 kit. The multiplex PCR reactions worked well for all the samples tested (data not shown).

The quality of the genomic DNA samples was also tested by real time PCR assays. Real time PCR experiments were done using Applied Biosystems 7900HT Fast Real Time PCR System. All the samples tested show very similar amplication profiles (FIG. 4).

The same purification process has been successfully applied to blood samples from other animals as well. High quality genomic DNA was isolated from different animals such as rat, Guinea pig, horse, chicken and sheep.

(E) Isolation of Genomic DNA from Tissue Samples

Figure 5:
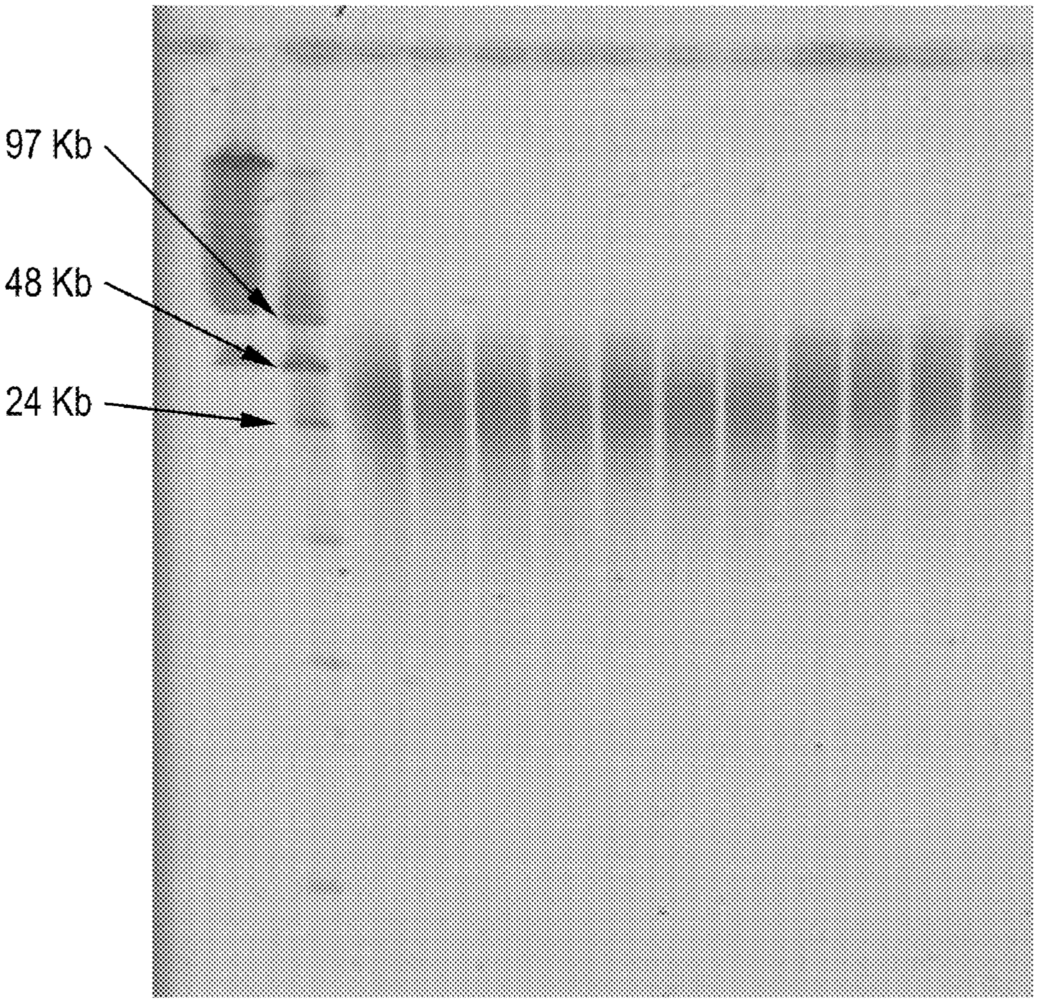
FIG. 5 shows pulse-field gel electrophoresis analysis of purified genomic DNA from 11 different rat liver samples. The DNA was isolated according to protocol (b). The left two lanes contain molecular weight markers with the relevant sizes labeled. It can be seen that the purified genomic DNA are all of large size.
Figure 6:
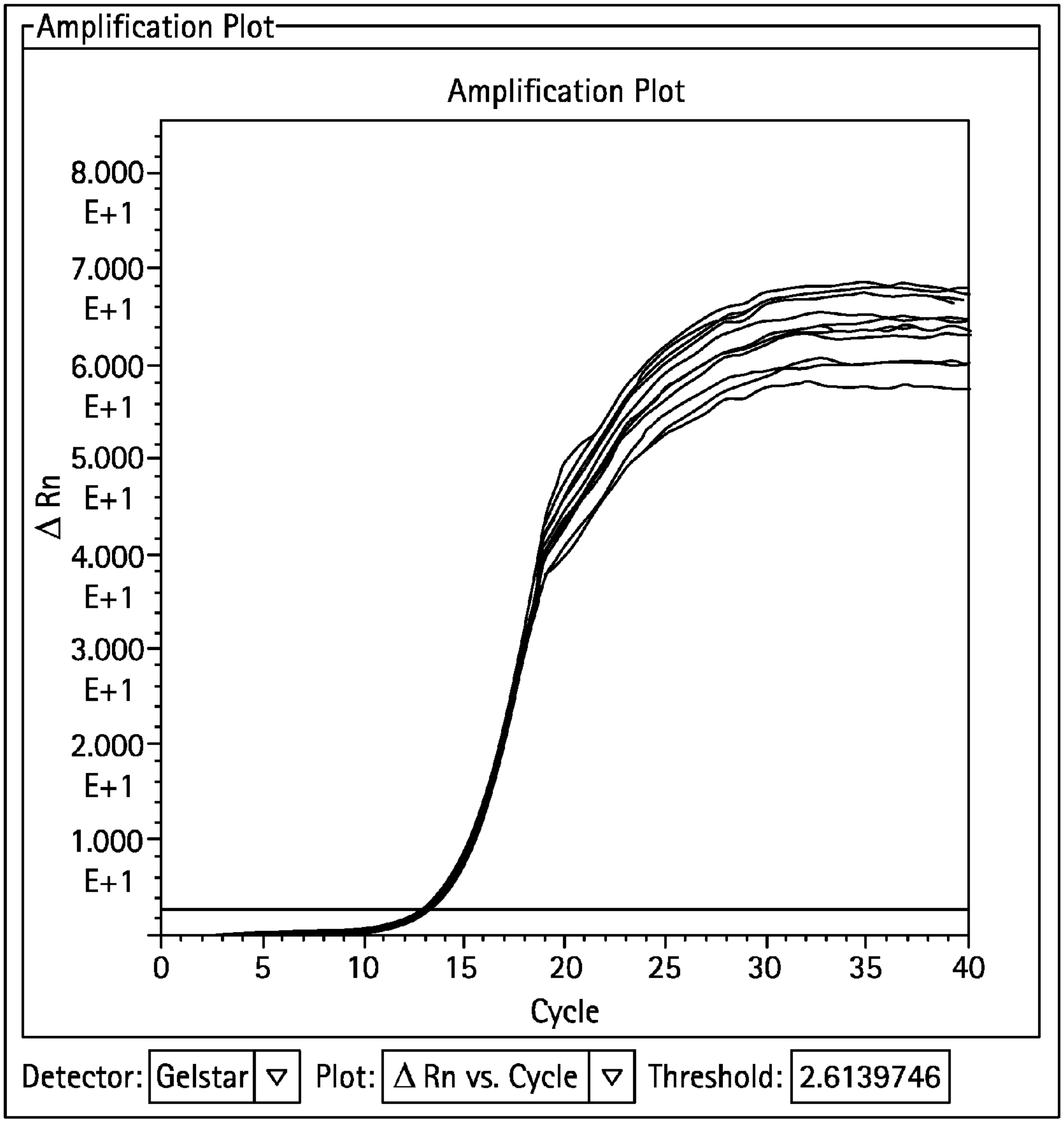
FIG. 6 shows real time PCR amplification results obtained from the genomic DNA samples shown in FIG. 1. Very similar amplification profiles can be observed among the samples, further demonstrating the quality of the genomic DNA samples.
Figure 7:
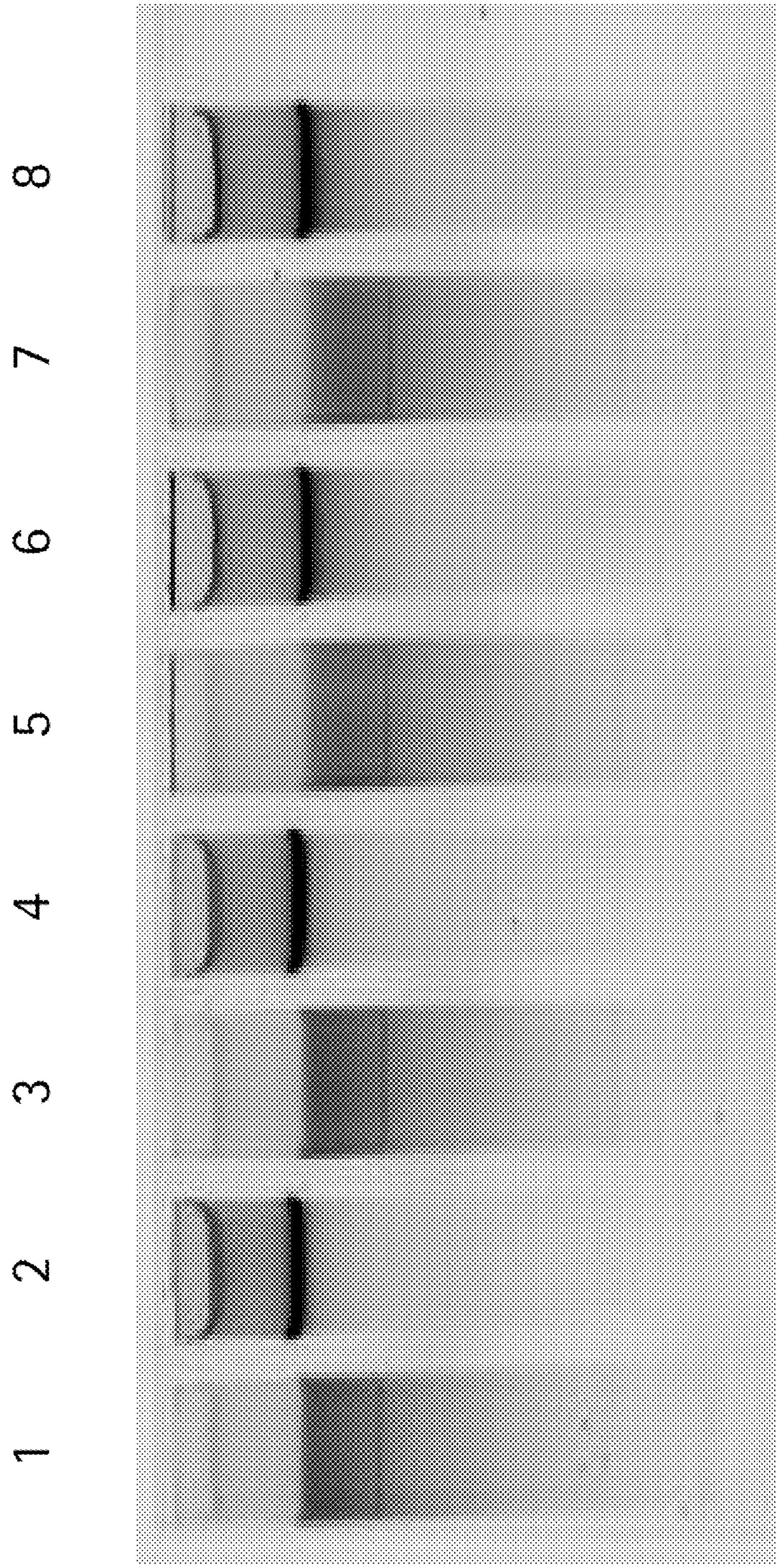
FIG. 7 is an agarose gel image that shows comparison of restriction enzyme (HindIII) digested and un-digested genomic DNA from 4 of the purified genomic DNA samples shown in FIG. 5. Lanes 2, 4, 6, 8 are undigested controls, while lanes 1, 3, 5, 7 are samples that have been digested, respectively. All the samples can be completely digested, further demonstrating the purity of the samples.

Two hundred milligrams of rat liver tissue was homogenized and lysed as described in the protocol section. The crude lysate was diluted with loading solution and centrifuged to pellet any particulates. The clear lysate was loaded on the ion-exchange purification column. After all the solution passed through the resin, 5 ml of loading solution was added to the column. When there was no more solution left on the top of the resin, 2.5 ml of elution solution (1M sodium chloride+0.5M potassium carbonate) was added to the column and the product was collected in the eluate. The genomic DNA thus obtained was desalted using NAP-25 column. The purity of the product was assessed by UV spectrophotometry and by gel analysis. Multiple samples were processed to access the consistency of the protocol. The size of the genomic DNA isolated was determined by Pulse Field Gel Electrophoresis (FIG. 5). The genomic DNA obtained by this method was also evaluated in downstream applications such as real time PCR (FIG. 6), and restriction digestion (FIG. 7).

By Pulse Field Gel Electrophoresis, it is clear that all the purified genomic DNA samples from rat liver tissue are of large size (FIG. 5). The purity of the sample was examined by an agarose gel analysis. It demonstrated that the genomic DNA isolated is pure and without RNA contamination (data not shown).

The quality of the purified genomic DNA was assessed by several methods.

The quality of the genomic DNA samples was tested by real time PCR assays. Real time PCR experiments were performed using Applied Biosystems 7900HT Fast Real Time PCR System. All the samples tested show very similar amplication profiles (FIG. 6).

The DNA was subjected to restriction enzyme digest using HindIII. Purified genomic DNA (250 ug) was digested with 40 units of the enzyme. The digested sample was analyzed on an agarose gel side-by-side with un-digested sample DNA. The gel image shows that all the genomic DNA was completely digested (FIG. 7, Lanes 2, 4, 6, 8 represent the purified, un-digested genomic DNA, while Lanes 1, 3, 5, 7 are samples digested with the enzyme).

(F) Isolation of Genomic DNA from Cell Cultures

Approximately $2\times10^7$ MRC5 cells were lysed using the procedure described in the protocols section. The crude lysate was diluted with loading solution and transferred to the ion-exchange purification column. After all the solution passed through the resin, 5 ml of loading solution was added to the column. When there was no more solution left on the top of the resin, 2.5 ml of elution solution was added to the column and the product was collected in the eluate. The genomic DNA thus obtained was desalted using NAP-25 column. The purity of the product was assessed by UV spectrophotometry and by gel analysis. The size of the genomic DNA isolated was determined by Pulse-Field Gel Electrophoresis. The genomic DNA obtained by this method was also evaluated in downstream applications such as real time PCR and restriction digestion.

Figure 8:
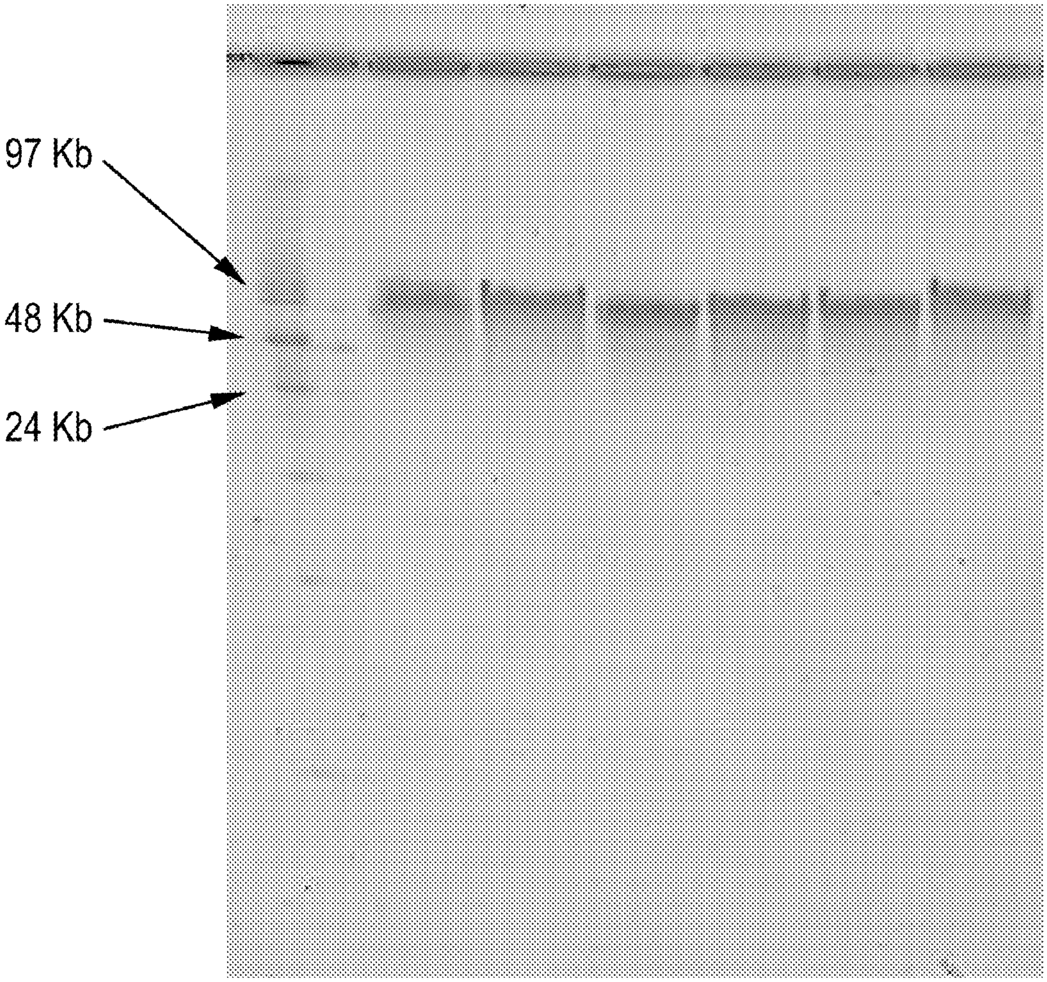
FIG. 8 shows pulse-field gel electrophoresis analysis of purified genomic DNA from 6 different cultured MRC5 cells samples. The DNA was isolated according to protocol (c). The left lane contains molecular weight markers with the relevant sizes labeled. It can be seen that the purified genomic DNA are all of large size, with the majority around 100 kb.

By Pulse Field Gel Electrophoresis, it is clear that all the purified genomic DNA samples from MRC5 cells are of large size (100Kb; FIG. 8). The purity of the sample was examined by an agarose gel analysis. It demonstrated that the genomic DNA isolated is pure and without RNA contamination (data not shown).

Figure 9:
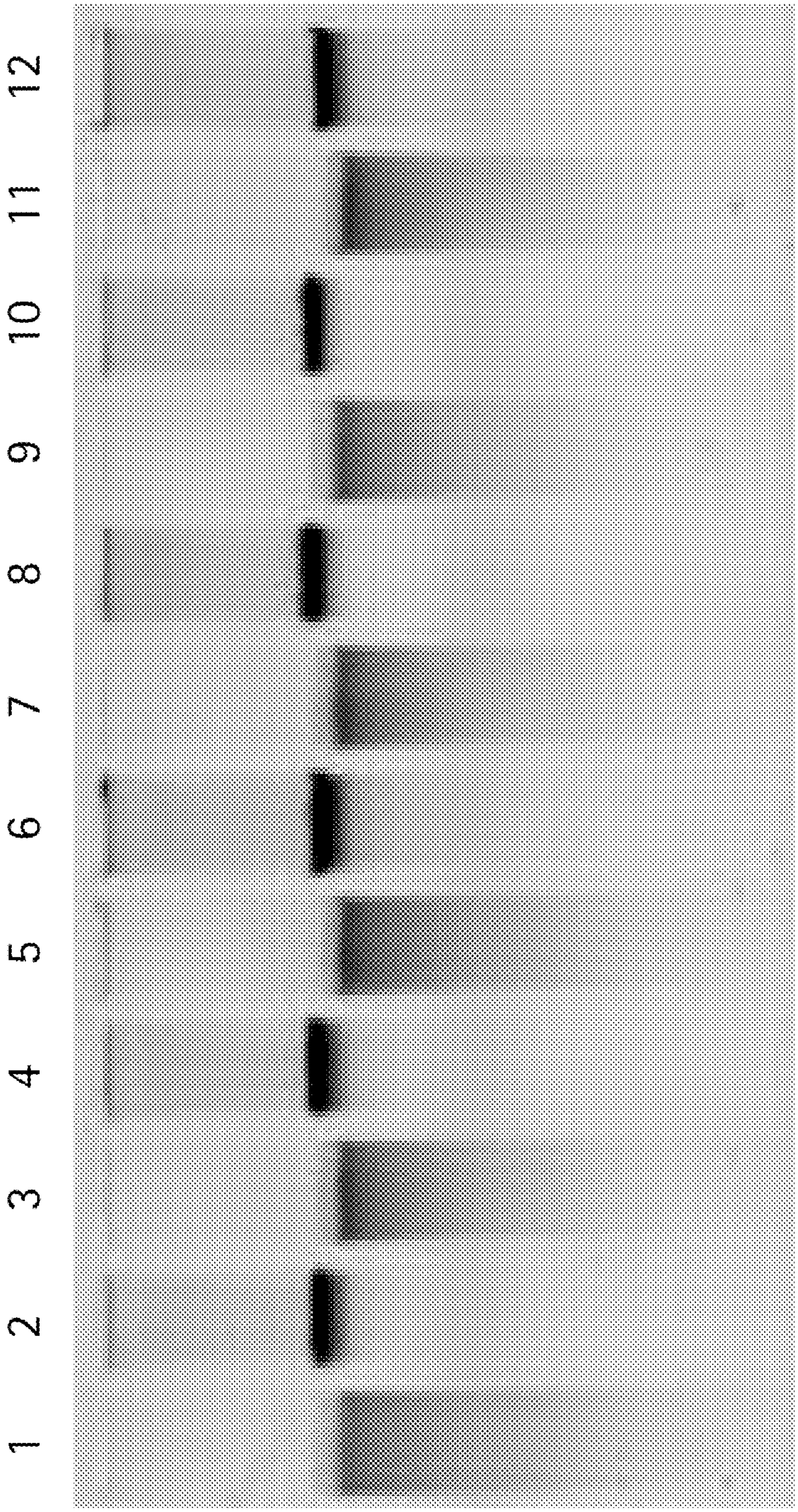
FIG. 9 is an agarose gel image that shows comparison of restriction enzyme (EcoRI) digested and un-digested genomic DNA from the purified genomic DNA samples shown in FIG. 8. Lanes 2, 4, 6, 8, 10 and 12 are undigested controls, while lanes 1, 3, 5, 7, 9 and 11 are samples that have been digested, respectively. All the samples can be completely digested, further demonstrating the purity of the samples.

The quality of the purified genomic DNA was assessed by restriction digest. The DNA was subjected to restriction enzyme digest using EcoRI. Purified genomic DNA (250 ug) was digested with 40 units of the enzyme. The digested sample was analyzed on an agarose gel side-by-side with un-digested sample DNA. The gel image shows that all the genomic DNA was completely digested (FIG. 9, Lanes 2, 4, 6, 8, 10, 12 represent the purified, un-digested genomic DNA, while Lanes 1, 3, 5, 7, 9, 11 are samples digested with the enzyme).

The present invention provides a kit for the separation and/or purification of a nucleic acid from a cellular sample, the kit comprising a lysis solution for generating an aqueous solution containing the nucleic acid from the; an anion exchanger bound to a solid support matrix for binding the nucleic acid; an elution solution for eluting the nucleic acid from the anion exchanger; and optionally desalting means for desalting said eluted nucleic acid. Suitably there is present in the elution solution an additive having the formula (I):

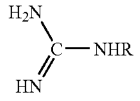

(I)

wherein:

R is a moiety selected from the group consisting of hydrogen, a lower alkyl, optionally substituted by amino, and the group:

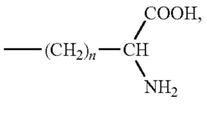

where n is 1, 2 or 3.

In one embodiment, the additive is arginine. In another embodiment the additive is guanidine present as its carbonate or bicarbonate salt.

Suitably, the anion exchanger is ANX fast flow resin. Alternatively the anion exchanger is DEAE Sephadex A-25 resin, Q-Sepharose fast flow resin, or Q-Sepharose XL, or CaptoQ resin.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A process for separating and/or purifying a genomic DNA, comprising:

a) contacting an aqueous solution containing the genomic DNA with an anion exchanger bound to a solid support matrix under conditions such that the anion exchanger binds the genomic DNA; and b) eluting the anion exchanger with an aqueous mobile phase comprising a basic genomic DNA elution salt solution;

wherein the basic elution salt solution comprises an additive having the formula (I):

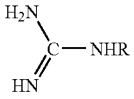

(I)

wherein:

R is a moiety selected from the group consisting of hydrogen, a lower alkyl, optionally substituted by amino, and the group:

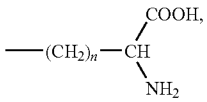

where n is 1, 2 or 3;

wherein the presence of the additive in the elution solution increases the pH of said aqueous mobile phase to between about pH 10 and about pH 13, and thereby provides an increase in the recovery of genomic DNA from the anion exchanger, as compared with the recovery of the genomic DNA from the same anion exchanger and in the absence of the additive in the elution solution, all other conditions being equal.

2. The process of claim 1, wherein R is selected from H, and lower alkyl.

3. The process of claim 2, wherein lower alkyl is a $C_1$ to $C_4$ alkyl group, preferably methyl or ethyl.

4. The process of claim 1, wherein said additive is a carbonate or bicarbonate salt.

5. The process of claim 1, wherein said additive is guanidine carbonate or guanidine bicarbonate.

6. The process of claim 1, wherein R is the group:

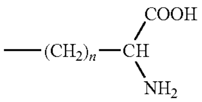

where n is 1, 2 or 3.

7. The process of claim 1, wherein said additive is arginine.

8. The process of claim 1, wherein said additive is present in the aqueous mobile phase at a concentration of between 0.1M and 2M.

9. The process of claim 8, wherein said additive is present in the aqueous mobile phase at a concentration of between 0.25M and 0.5M.

10. The process of claim 8, wherein said additive is present in the aqueous mobile phase at a concentration of about 0.5M.

11. The process of claim 1, wherein the pH of said aqueous mobile phase is between about pH 10.5 and about pH 11.6.

12. The process of claim 1, wherein the presence of said additive in the aqueous mobile phase provides an increase in the recovery of genomic DNA from the anion exchanger of at least 40%, as compared with the recovery of said genomic DNA from the same anion exchanger and in the absence of said additive in said elution solution, all other conditions being equal.

13. The process of claim 1, wherein the presence of said additive in the aqueous mobile phase provides an increase in the recovery of genomic DNA from the anion exchanger of between about 40% and about 400%, as compared with the recovery of said genomic DNA from the same anion exchanger and in the absence of additive in said elution solution, all other conditions being equal.

14. A kit for the separation and/or purification of a genomic DNA from a cellular sample, said kit comprising:

a) a lysis solution for generating an aqueous solution containing the genomic DNA from said cellular sample;

b) an anion exchanger bound to a solid support matrix for binding the genomic DNA;

c) a basic elution salt solution for eluting the genomic DNA from said anion exchanger; and d) a desalting column for desalting said eluted genomic DNA;

wherein there is present in said elution solution an additive having the formula (I):

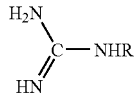

(I)

wherein:

R is a moiety selected from the group consisting of hydrogen, a lower alkyl, optionally substituted by amino, and the group:

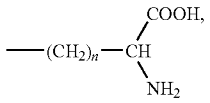

where n is 1, 2 or 3.

15. The kit of claim 14, wherein the additive is arginine.

16. The kit of claim 14, wherein the additive is guanidine carbonate or bicarbonate salt.

* * * * *